US011911792B2

(12) United States Patent
Bardhan Roy et al.

(10) Patent No.: US 11,911,792 B2
(45) Date of Patent: Feb. 27, 2024

(54) MICROMACHINED ULTRASONIC TRANSOURCES WITH DUAL OUT-OF-PLANE AND IN-PLANE ACTUATION AND DISPLACEMENT

(71) Applicant: GE PRECISION HEALTHCARE LLC, Wauwatosa, WI (US)

(72) Inventors: Rupak Bardhan Roy, Nice (FR);
Edouard Da Cruz, Nice (FR);
Frederic Lanteri, Le Cannet (FR);
Omid Farhanieh, Antibes (FR);
Jean-François Gelly, Mougins (FR);
Flavien Daloz, Biot (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 625 days.

(21) Appl. No.: 17/146,991

(22) Filed: Jan. 12, 2021

(65) Prior Publication Data

US 2022/0219198 A1    Jul. 14, 2022

(51) Int. Cl.
   *B60B 1/02*  (2006.01)
   *B81B 3/00*  (2006.01)
   *H02N 1/00*  (2006.01)
   *B06B 1/02*  (2006.01)

(52) U.S. Cl.
   CPC .......... *B06B 1/0292* (2013.01); *B06B 1/0207* (2013.01); *B81B 3/0021* (2013.01); *H02N 1/006* (2013.01); *B06B 2201/51* (2013.01)

(58) Field of Classification Search
   CPC . B60B 1/0207; B60B 1/0292; B60B 2201/51; B81B 3/0021; H02N 1/006
   See application file for complete search history.

(56) References Cited

U.S. PATENT DOCUMENTS

| 8,526,271 | B2 | 9/2013 | Huang | |
| 10,092,270 | B2 | 10/2018 | Dirksen | |
| 2009/0167107 | A1* | 7/2009 | Huang | H03H 9/2405 |
| | | | | 310/300 |
| 2011/0040189 | A1 | 2/2011 | Petruzzello et al. | |
| 2011/0050033 | A1* | 3/2011 | Nikoozadeh | B06B 1/0292 |
| | | | | 310/300 |
| 2012/0086087 | A1 | 4/2012 | Fitzpatrick | |

(Continued)

FOREIGN PATENT DOCUMENTS

WO    WO-2016080931 A1 *  5/2016  ........... B06B 1/0292

OTHER PUBLICATIONS

U.S. Appl. No. 16/881,341, filed May 22, 2020, Rupak Bardhan Roy.

*Primary Examiner* — Eric Johnson
(74) *Attorney, Agent, or Firm* — Fletcher Yoder, P.C.

(57) ABSTRACT

A capacitive transducer is provided. The capacitive transducer includes a plate including a protruding center mass and a substrate with a center depression configured to accept the center mass. The capacitive transducer also includes a first electrode coupled to a non-horizontal edge surface of the center mass and a second electrode coupled to a non-horizontal edge surface of the center depression. The capacitive transducer further includes a third electrode coupled to a horizontal edge surface of the center mass and a fourth electrode coupled to a horizontal edge surface of the center depression. The plate is coupled to the substrate at least along an outer perimeter area of the plate and the substrate.

20 Claims, 11 Drawing Sheets

(56) References Cited

U.S. PATENT DOCUMENTS

| | | | |
|---|---|---|---|
| 2015/0078590 A1* | 3/2015 | Daley | H04R 17/005 |
| | | | 381/190 |
| 2016/0199030 A1 | 7/2016 | Patil et al. | |
| 2017/0165715 A1 | 6/2017 | Sudol et al. | |
| 2017/0320091 A1 | 11/2017 | Budzelaar et al. | |
| 2021/0362188 A1* | 11/2021 | Bardhan Roy | B06B 1/0292 |

* cited by examiner

MICROMACHINED ULTRASONIC TRANSOURCES WITH DUAL OUT-OF-PLANE AND IN-PLANE ACTUATION AND DISPLACEMENT

BACKGROUND

The subject matter disclosed herein relates to transducers and, in particular, micromachined ultrasonic transducers with dual out-of-plane and in-plane actuation and displacement.

An ultrasound device may be used for imaging targets such as organs and soft tissues in a human body, as well non-human targets. For example, an ultrasound device may be used for applications such as ultrasound/acoustic sensing, non-destructive evaluation (NDE), ultrasound therapy (e.g., High Intensity Focused Ultrasound (HIFU)), etc., in addition to ultrasound imaging of humans, animals, etc.

Ultrasound devices may use real time, non-invasive high frequency sound waves to produce a series of two-dimensional (2D) and/or three-dimensional (3D) images. The sound waves may be transmitted by a transmit transducer, and the reflections of the transmitted sound waves may be received by a receive transducer. The received sound waves may then be processed to display an image of the target. A conventional capacitive micromachined ultrasound transducer (CMUT) that is used as a transmit transducer and/or a receive transducer may include a top electrode and a bottom electrode, where the top electrode may move due to electrical signals to generate sound waves, or move due to receiving sound waves to generate electrical signals that can be processed. The top electrode and the bottom electrode may be separated by a gap, where the gap may comprise some level of vacuum or the gap may be filled with, for example, air. However, conventional and traditional CMUTs may have certain limitations or disadvantages.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a capacitive transducer is provided. The capacitive transducer includes a plate including a protruding center mass and a substrate with a center depression configured to accept the center mass. The capacitive transducer includes a first electrode coupled to a non-horizontal edge surface of the center mass and a second electrode coupled to a non-horizontal edge surface of the center depression. The capacitive transducer further includes a third electrode coupled to a horizontal edge surface of the center mass and a fourth electrode coupled to a horizontal edge surface of the center depression. The plate is coupled to the substrate at least along an outer perimeter area of the plate and the substrate.

In accordance with a second embodiment, a system is provided. The system includes a capacitive transducer. The capacitive transducer includes a plate including a protruding center mass and a substrate with a center depression configured to accept the center mass. The capacitive transducer further includes a first pair of electrodes arranged on non-horizontal surfaces of the capacitive transducer and a second pair of electrodes arranged on horizontal surfaces of the capacitive transducer. The system also includes circuitry configured to actuate the capacitive transducer by applying a direct current (DC) signal to the first pair of electrodes and applying an alternative current (AC) signal to the second pair of electrodes.

In accordance with a third embodiment, a capacitive transducer is provided. The capacitive transducer includes a plate including a protruding center mass and a substrate with a center depression configured to accept the center mass. The capacitive transducer also includes a first electrode coupled to a non-horizontal edge surface of the center mass and a second electrode coupled to a non-horizontal edge surface of the center depression. The capacitive transducer further includes a third electrode coupled to a horizontal edge surface of the center mass and a fourth electrode coupled to a horizontal edge surface of the center depression. The capacitive transducer even further includes a first insulation layer disposed on a portion of the third electrode, a second insulation layer disposed on a portion of the fourth electrode, or both the first insulation layer disposed on the portion of the third electrode and the second insulation layer disposed on the portion of the fourth electrode.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
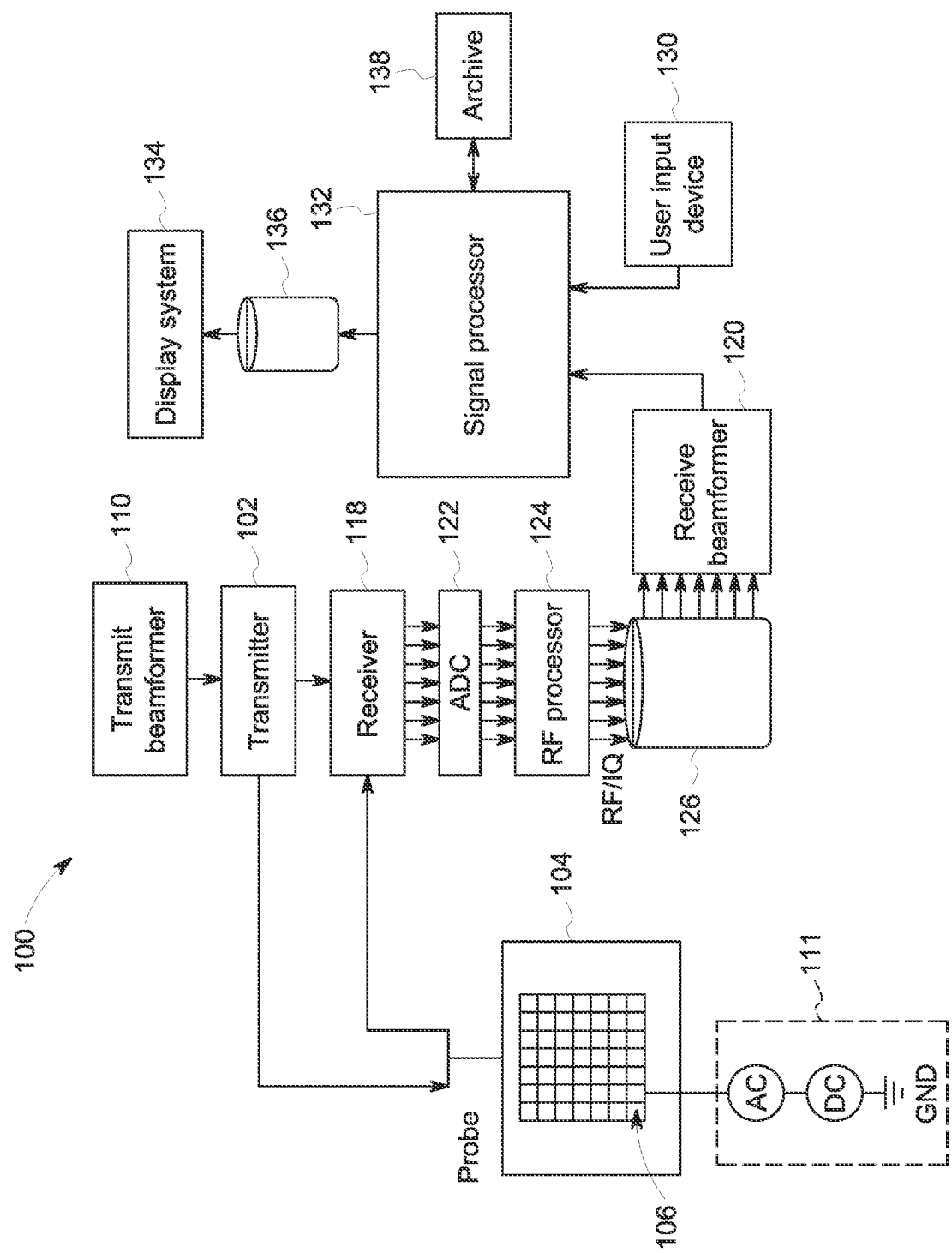
FIG. 1 is a block diagram of an exemplary ultrasound system that may be used in ultrasound imaging, in accordance with various embodiments.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The presently contemplated embodiments provide micromachined ultrasonic transducers (e.g. CMUTs) with dual out-of-plane and in-plane actuation and displacement. In particular, a direct current (DC) signal or bias may be applied to a pair of vertical electrodes (e.g., for out-of-plane actuation) and an alternative current signal applied to a pair of horizontal electrodes (e.g., for in plane actuation). Actuation with the DC signal is orthogonal to a direction of displacement of a center mass of a plate toward a depression of a substrate, while actuation with the AC signal is parallel to the direction of displacement. The in-plane actuation with the AC signal increases the electromechanical coupling factor. This enables the CMUTs to have a higher transmit bandwidth when the DC signal is applied to the pair of vertical electrodes and the AC signal is applied to the pair of horizontal or in-plane electrodes as opposed to when both the AC and DC signals are applied to vertical pair of electrodes. The disclosed CMUTS can operate in both a conventional mode of operation and a mechanical collapse mode of operation (e.g., when the center mass of the plate contacts the substrate). Also, the disclosed CMUTs can operate in different drive configurations. For example, during operation in a transmit mode, only an AC signal may be applied to the pair of horizontal electrodes without a DC bias or an AC current signal being applied to the pair of vertical electrodes. Also, during operation in transmit and receive mode, the DC signal may be applied to either the pair of vertical electrodes or the pair of horizontal electrodes. For example, during the transmit portion of the transmit and receive mode, the DC signal may be applied to the pair of vertical electrodes and the AC signal applied to the pair of horizontal electrodes, while, during the receive portion of the transmit and receive mode, both the AC and DC signals may be applied to the pair of horizontal electrodes.

While a CMUT can be used for medical imaging, the CMUT may also be used for various other purposes such as, for example, ultrasound/acoustic sensing, non-destructive evaluation (NDE), ultrasound therapy (e.g., High Intensity Focused Ultrasound (HIFU)), etc., in addition to ultrasound imaging of humans or animals.

As used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

FIG. 1 is a block diagram of an exemplary ultrasound system that may be used in ultrasound imaging, in accordance with various embodiments. Referring to FIG. 1, there is shown a block diagram of an exemplary ultrasound system 100. The ultrasound system 100 comprises a transmitter 102, an ultrasound probe 104, a transmit beamformer 110, a receiver 118, a receive beamformer 120, A/D converters 122, an RF processor 124, an RF/IQ buffer 126, a user input device 130, a signal processor 132, an image buffer 136, a display system 134, and an archive 138. The circuit 111 is a typical example of bias of a cMUT but many options are described in public literature.

The transmitter 102 may comprise suitable logic, circuitry, interfaces and/or code that may be operable to drive the ultrasound probe 104. The ultrasound probe 104 may comprise, for example, a single element CMUT, a 1D array of CMUTs, 2D array of CMUTs, an annular (ring) array of CMUTs, etc. Accordingly, the ultrasound probe 104 may comprise a group of transducer elements 106 that may be, for example, CMUTs. In certain embodiments, the ultrasound probe 104 may be operable to acquire ultrasound image data covering, for example, at least a substantial portion of an anatomy, such as the heart, a blood vessel, or any suitable anatomical structure. Each of the transducer elements 106 may be referred to as a channel.

The transmit beamformer 110 may comprise suitable logic, circuitry, interfaces and/or code that may be operable to control the transmitter 102 that drives the group of transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes can then be received by the transducer elements 106. For example, one or more drive circuits 111 may be coupled to and drive or control the electrodes of each transducer element 106. For example, the one or more drive circuits may be coupled to separate AC and DC voltage sources.

The group of transducer elements 106 in the ultrasound probe 104 may be operable to convert the received echoes into analog signals and communicated to a receiver 118. The receiver 118 may comprise suitable logic, circuitry, interfaces and/or code that may be operable to receive the signals from the ultrasound probe 104. The analog signals may be communicated to one or more of the plurality of A/D converters 122.

Accordingly, the ultrasound system 100 may multiplex such that ultrasonic transmit signals are transmitted during certain time periods and echoes of those ultrasonic signals are received during other time periods. Although not shown explicitly, various embodiments of the disclosure may allow simultaneous transmission of ultrasonic signals and reception of echoes from those signals. In such cases, the probe may comprise transmit transducer elements and receive transducer elements.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF data, which may be, for example, I/Q signal data, real valued RF data, etc., may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

Accordingly, various embodiments may have, for example, the RF processor 124 process real valued RF data, or any other equivalent representation of the data, with an appropriate RF buffer 126.

The receive beamformer 120 may comprise suitable logic, circuitry, interfaces and/or code that may be operable to perform digital beamforming processing to sum, for example, delayed, phase shifted, and/or weighted channel signals received from the RF processor 124 via the RF/IQ buffer 126 and output a beam summed signal. The delayed, phase shifted, and/or weighted channel data may be summed to form a scan line output from the receive beamformer 120, where the scan line may be, for example, complex valued or non-complex valued. The specific delay for a channel may be provided, for example, by the RF processor 124 or any other processor configured to perform the task. The delayed, phase shifted, and/or weighted channel data may be referred to as delay aligned channel data.

The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 may comprise a plurality of receive beamformers 120.

The user input device 130 may be utilized to input patient data, scan parameters, settings, select protocols and/or templates, and the like. In an exemplary embodiment, the user input device 130 may be operable to configure, manage, and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include switch(es), button(s), rotary encoder(s), a touchscreen, motion tracking, voice recognition, a mouse device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may comprise a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in a live or off-line operation. In various embodiments, the processed image data can be presented at the display system 134 and/or stored at the archive 138. The archive 138 may be a local archive, a Picture Archiving and Communication System (PACS), or any suitable device for storing images and related information.

The signal processor 132 may comprise one or more central processing units, microprocessors, microcontrollers, and/or the like. The signal processor 132 may be an integrated component, or may be distributed across various locations, for example. In an exemplary embodiment, the signal processor 132 may be capable of receiving input information from the user input device 130 and/or the archive 138, generating an output displayable by the display system 134, and manipulating the output in response to input information from the user input device 130, among other things. The signal processor 132 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates may range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes worth of frames of ultrasound scan data. The frames of ultrasound scan data are stored in a manner to facilitate retrieval thereof according to its order or time of acquisition. The image buffer 136 may be embodied as any known data storage medium.

The display system 134 may be any device capable of communicating visual information to a user. For example, a display system 134 may include a liquid crystal display, a light emitting diode display, and/or any suitable display or displays. The display system 134 can be operable to present ultrasound images and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display. Additionally, while the ultrasound system 100 was described to comprise a receive beamformer 120, an RF processor 124, and a signal processor 132, various embodiments of the disclosure may use various number of processors. For example, various devices that execute code may be referred to generally as processors. Various embodiments may refer to each of these devices, including each of the RF processor 124 and the signal processor 132, as a processor. Furthermore, there may be other processors to additionally perform the tasks described as being performed by these devices, including the receive beamformer 120, the RF processor 124, and the signal processor 132, and all of these processors may be referred to as a "processor" for ease of description.

Conventional CMUTs include two plates separated by either a vacuum or fluid gap. The plates are biased by a DC voltage and then superimposed with the AC signal of chosen frequency and amplitude. The working principle of CMUTs is based on Coulomb's laws of attraction. During the DC bias the electrostatic force and the mechanical restorative balance each other which keeps the membrane at the targeted displaced location. However, at a certain DC bias voltage, the electrostatic forces surpass the restorative force and the membrane touches the bottom electrode. For perfectly clamped CMUT plates, this physical phenomenon occurs at substantially ⅓rd of the effective gap height. The distance is called pull-in or collapse distance and voltage at which the phenomenon happens is called collapse or pull-in voltage. Operating the device in collapse mode provides higher levels of acoustic power and wider bandwidth during operation. One or more insulation layers may be sandwiched between the active membrane (top electrode), gap (vacuum or fluid) and the back-support structure (with bottom electrode) such that no short-circuit occurs during such collapse phenomenon.

The equation for collapsed voltage $V_{col}$ is shown below in Equations 1 and 2 (example of flat rigid condenser model):

$$V_{col} = \sqrt{\frac{8Kg_{eff}^3}{27\varepsilon_0 A}} \quad \text{(Equation 1)}$$

where, K is membrane stiffness, $\varepsilon_0$ is permittivity of free space, and A is the device area. The effective gap height is given by:

$$g_{eff} = g_0 + \frac{t_i}{\varepsilon_i} \quad \text{(Equation 2)}$$

where $g_0$ is the vacuum/air gap, $t_i$ is the insulation layer thickness, and $\varepsilon_i$ is the permittivity of the insulation layer material.

In the following figures, it should be noted that the terms vertical and horizontal are defined relative to a longitudinal axis or length of the CMUT devices (e.g., extending in the X-direction). Thus, a vertical direction would be orthogonal to a longitudinal axis or length of a CMUT device and a horizontal direction would be parallel to a longitudinal axis or length of a CMUT device.

Figure 2A:
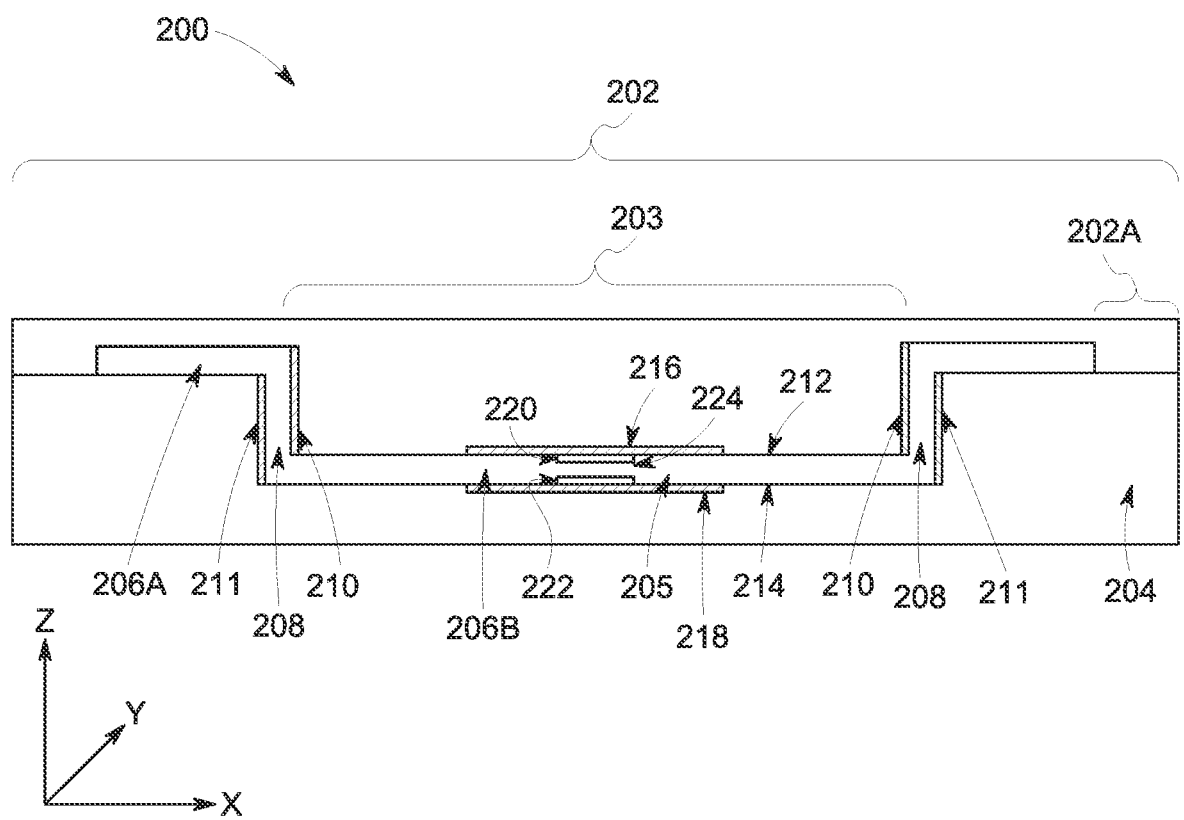
FIGS. 2A and 2B illustrate cross-sections of configurations for example capacitive micromachined ultrasound transducers (CMUTs) with dual out-of-plane and in-plane actuation and displacement, in accordance with various embodiments.

FIG. 2A illustrates a cross-section of a configuration for an example CMUT with dual out-of-plane and in-plane actuation and displacement, in accordance with various embodiments. Referring to FIG. 2, there is shown a CMUT 200 comprising a plate 202 and a substrate 204. The plate 202 may comprise a center mass 203. The center mass 203 protrudes down into a depression 205 in a corresponding area of the substrate 204. The substantially vertical edges (or non-horizontal edges) of the center mass 203 include electrode(s) 210 and the substantially vertical edges of the depression 205 include electrode(s) 211. A bottom surface 212 of the center mass 203 faces a top surface 214 of the depression 205. The substantially horizontal edge of the bottom surface 212 includes electrode 216 and the substantially horizontal edge of the top surface 214 includes electrode 218. While not shown, when viewed from the top at the X-Y plane, the electrodes 216, 218 may have a circular shape (as shown with electrodes 1301 and 1401 in FIGS. 7 and 8, respectively), a rectangular shape, or any other shape. The electrodes 210, 211 and the electrodes 216, 218 may be provided with electrical signals (DC bias and AC signal) used to move the plate 202 in the Z direction to generate sonic waves. The CMUT 200 may operate in transmit mode (Tx), receive (Rx) mode, and/or transmit and receive (Tx-Rx) mode. In addition, the CMUT 200 may operate in a conventional mode or mechanical collapse mode (e.g., when the bottom surface 212 contacts the top surface 214 of the depression 205). Different drive configurations may be utilized for the CMUT 200. For example, DC bias may applied to either the electrodes 210, 211 (fringe electrodes) or the electrodes 216, 218 (in-plane electrodes or central electrodes). For example, during operation of the CMUT 200 in the Tx-Rx mode, a DC bias signal is applied to the electrodes 210 and 211 and an AC signal applied only to the electrodes 216 and 218 during the transmit portion, while during the receive portion both the DC bias signal and the AC signal are applied to the electrodes 210 and 211. In such a configuration, different DC voltage levels may be applied to the respective electrode pairs (electrodes 210, 211 and electrodes 216, 218) during transmitting, receiving, or both transmitting and receiving. During operation of the CMUT 200 in the Tx mode, only the AC signal may be applied to the electrodes 216, 218 without the DC signal applied to either of the electrodes pairs (electrodes 210, 211 and electrodes 216, 218). In this scenario, the CMUT 200 may be driven at half the targeted frequency to receive the harmonic at the output. In the Rx mode, both the DC bias signal and the AC signal are applied to the electrodes 210 and 211.

One or more insulation layers or bumps or high contact resistance layers or bumps may be sandwiched between the electrodes 216, 218 in case of mechanical collapse or accidental contact to avoid a short circuit. As depicted, an insulation layer or bump 220 (or high contact resistance layer or bump) is disposed on a portion of the electrode 216 and an insulation layer or bump 222 (or high contact resistance layer or bump) is disposed on a portion of the electrode 218. In certain embodiments, only the insulation layer or bump 220 (or high contact resistance layer or bump) is disposed on the electrode 216. In other embodiments, only the insulation layer or bump 222 (or high contact resistance layer or bump) is disposed on the electrode 218.

The plate 202 may be coupled to the substrate 204 at the outer perimeter area 202A of the plate 202. The coupling may be via any appropriate methods, including processes known in MEMS fabrication, such as, for example, wafer bonding.

It may be seen that the CMUT 200 has an upper vertical gap 206A and a lower vertical gap 206B between the plate 202 and the substrate 204. There is also a horizontal gap 208 between the electrodes 210 and 211. Further, there is a vertical gap 224 between the electrodes 216 and 218 (and respective insulation layers 220 and 222 or high contact resistance layers). The horizontal gap 208 and the vertical gap 224 may be referred to as an electrode gap 208 and an electrode gap 224. When the DC bias is applied to the electrodes 210, 211 and the AC signal is applied to the electrodes 216, 218 (i.e., dual mode actuation), the vertical gaps 206A and 206B are the actuation boundaries making the AC signal parallel to the device displacement direction along the Z axis and the DC bias orthogonal to the device displacement direction along the Z-axis. When both the DC bias and the AC signal are applied to the electrodes (i.e., fringe mode activation), the vertical gaps 206A and 206B are the actuation boundaries making the DC bias and the AC signal orthogonal to the device displacement direction along the Z axis. Operation in dual mode actuation improves electromechanical coupling as opposed to fringe mode operation. While not shown, when viewed from the top at the X-Y plane, the CMUT 200 may have a circular shape, a rectangular shape, or any other shape.

Figure 2B:
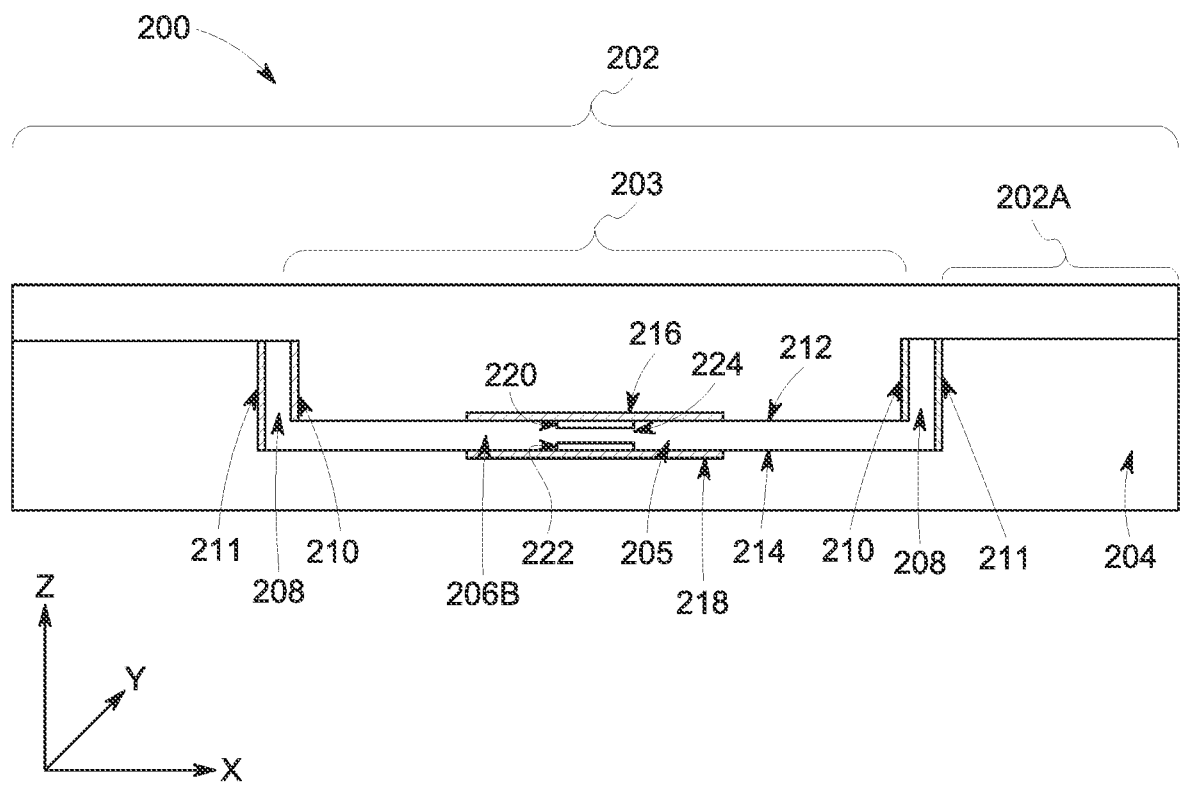

Since the CMUT plate 202 has a mechanical constraint in the X direction due to clamping at the edges (outer perimeter area 202A of the plate 202), the displacement degree of freedom may be predominantly in the Z direction. Accordingly, even though the actuation is in the X-direction (e.g., during fringe mode actuation and by DC bias in the dual mode actuation), the X-direction displacement may be much less than the Z-direction displacement due to the mechanical constraint. Various embodiments of the disclosure may have, for example, a displacement ratio of 10 or more for Z-direction displacement versus X-direction displacement. It may be noted that the displacement ratio may be determined for specific usage for the CMUT 200. FIG. 2B illustrates an alternative embodiment for the CMUT having a larger outer perimeter area 202A where the plate 202 is coupled to the substrate 204.

Figure 3:
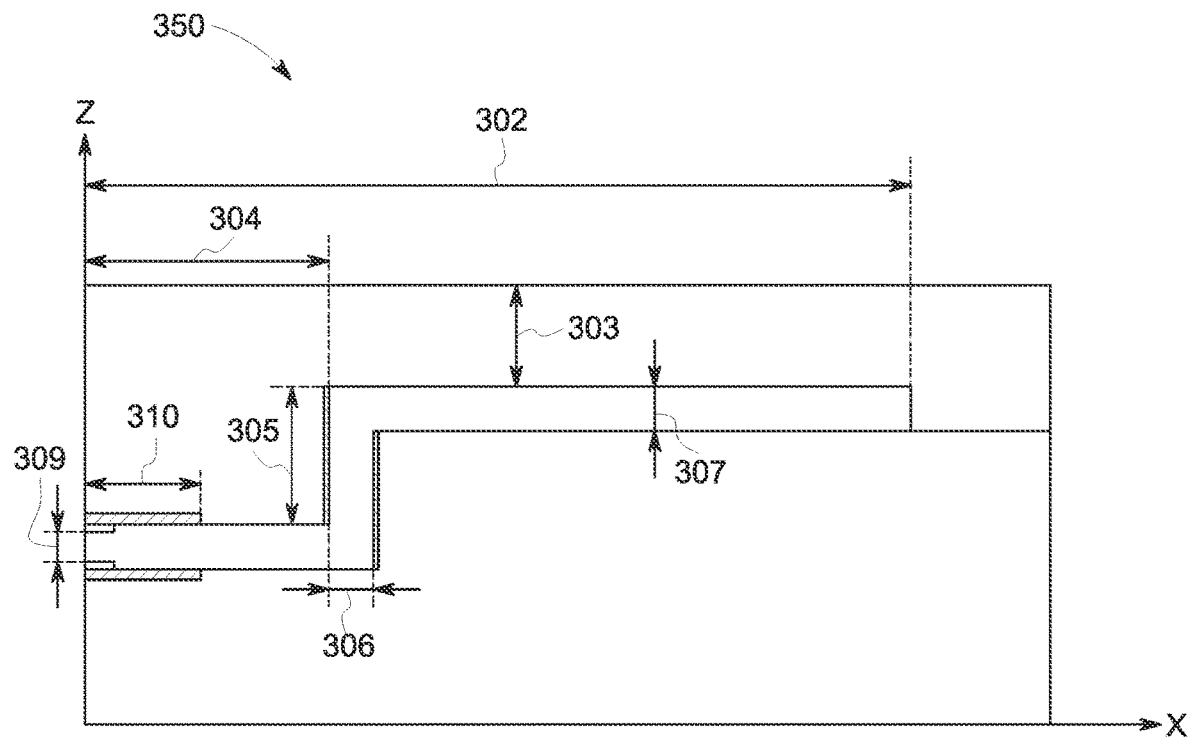
FIG. 3 illustrates example applicable dimensions of the example CMUT of FIG. 2, in accordance with various embodiments.

FIG. 3 illustrates example applicable dimensions of the example CMUT of FIG. 2, in accordance with various embodiments. Referring to FIG. 3, there is shown a partial view of a CMUT 300 that may be similar to the CMUT 200. The dimensions may include, for example, a plate radius ($P_r$) 302, a mass radius ($M_r$) 304, a horizontal gap ($G_h$) 306, vertical gaps ($G_v$) 307 and 309, a mass thickness ($M_t$) 305, a plate thickness ($P_t$) 303, an in-plane electrode radius ($Eip_R$) or electrode coverage area (EC) 310. The horizontal gap 306 and the vertical gap 309 may be referred to as the electrode gap 306 and the electrode gap 309, respectively. The vertical gap 309 is defined as the gap between the any insulation layers (e.g., insulation layers 220 and/or 222) disposed on and between the in-plane electrodes (e.g., electrodes 216 and 218 in FIG. 2).

The vertical gaps ($G_v$) 307 and 309 may be equal to each other. The vertical gap ($G_v$) 307 and/or 309 may be equal to the horizontal gap ($G_h$) 306. The vertical gap ($G_v$) 307 and/or 309 may be greater or smaller than the horizontal gap ($G_h$) 306. The various gaps may be measured in any appropriate units such as, for example, microns, nanometers, etc.

A term "$E_{PI}$" may be a voltage for electrical pull-in, or the DC bias needed to make the side electrodes collapse to each other in the X-direction. A term "$E_{MC}$" may be used for voltage needed for mechanical collapse. Mechanical collapse is defined as the phenomenon when at a certain DC bias the center mass 203 touches the bottom of the depression 205 of the substrate 204.

The $E_{MC}$ among various embodiments may vary due to differences in the above parameters. For example, the CMUT 300 may have the following dimensions: $P_r$ of 50 μm, $M_r$ of $P_r/3$, $P_t$ of 300 nm, $M_t$ of $2*G_v$, $G_v$ of 100 nm, $G_h$ of $0.2*G_v$. These dimensions may result in an $E_{MC}$ of 34 volts (V). Increasing the ratio of the plate radius, $P_r$, to the mass radius, $M_r$, may result (e.g., to $P_r/M_r$ of 2) in increasing the $E_{MC}$ (e.g., to 36 V). Decreasing the ratio of the plate radius, $P_r$, to the mass radius, $M_r$, may result (e.g., to $P_r/M_r$ of 4) in decreasing the $E_{MC}$ (e.g., to 30 V). Eliminating the vertical gap 307 (e.g., between the plate 202 and the substrate 204, as depicted in the CMUT 350 in FIG. 4, may significantly increase the $E_{MC}$ (e.g., to 182 V). The $E_{MC}$ may also vary depending on the materials used for the different layers.

Figure 5:
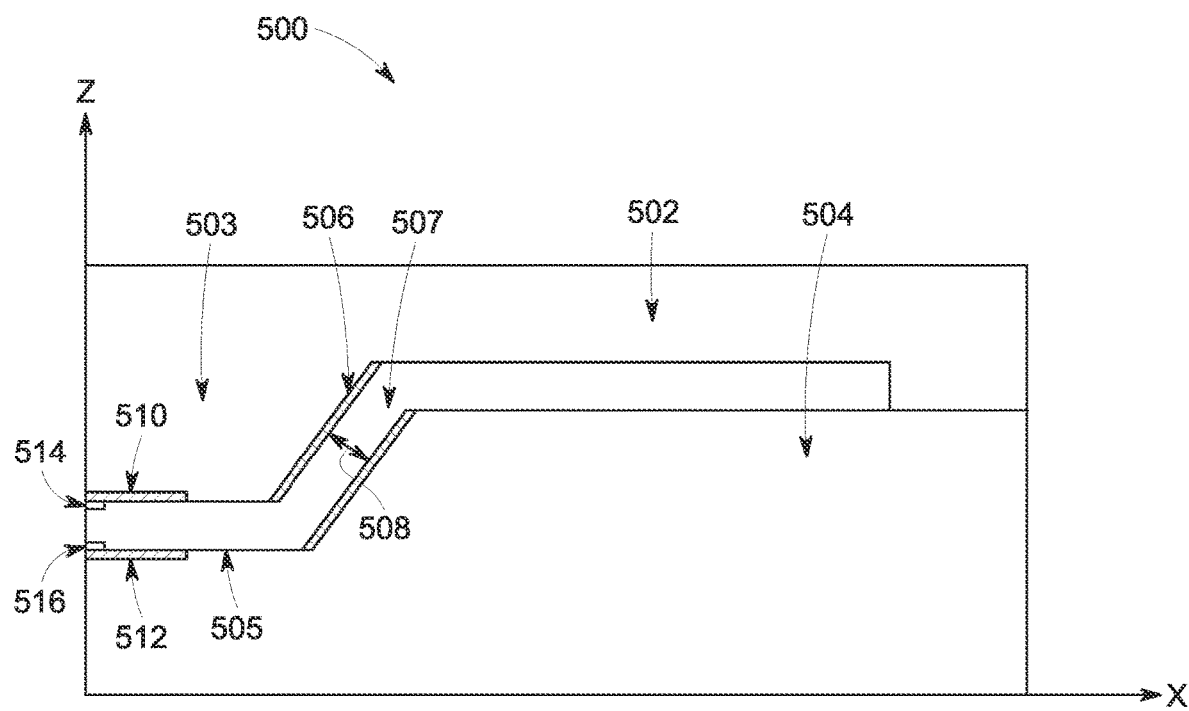
FIG. 5 illustrates another configuration for an example CMUT with dual out-of-plane and in-plane actuation and displacement, in accordance with various embodiments.

FIG. 5 illustrates another configuration for an example CMUT with dual out-of-plane and in-plane actuation and displacement, in accordance with various embodiments. Referring to FIG. 5, there is shown a CMUT 500 that is similar to the CMUT 200, except that the edges of the center mass 503 of the plate 502 and the edges of the depression 505 of the substrate 504 are diagonal. Accordingly, orientation of the electrodes 506 and 507 are also diagonal. The diagonal edges may also be referred to as non-horizontal edges where the angle of inclination (θ) is greater than 0 degrees (e.g., conventional device) and less than 90 degrees (e.g., fringe device). The orthogonal distance between the electrodes 506 and 507 may be referred to as the electrode gap 508. Similar to CMUT 200, the CMUT 500 includes horizontal or in-plane electrodes 510 and 512 and respective insulation layers 514 and 516.

Figure 6:
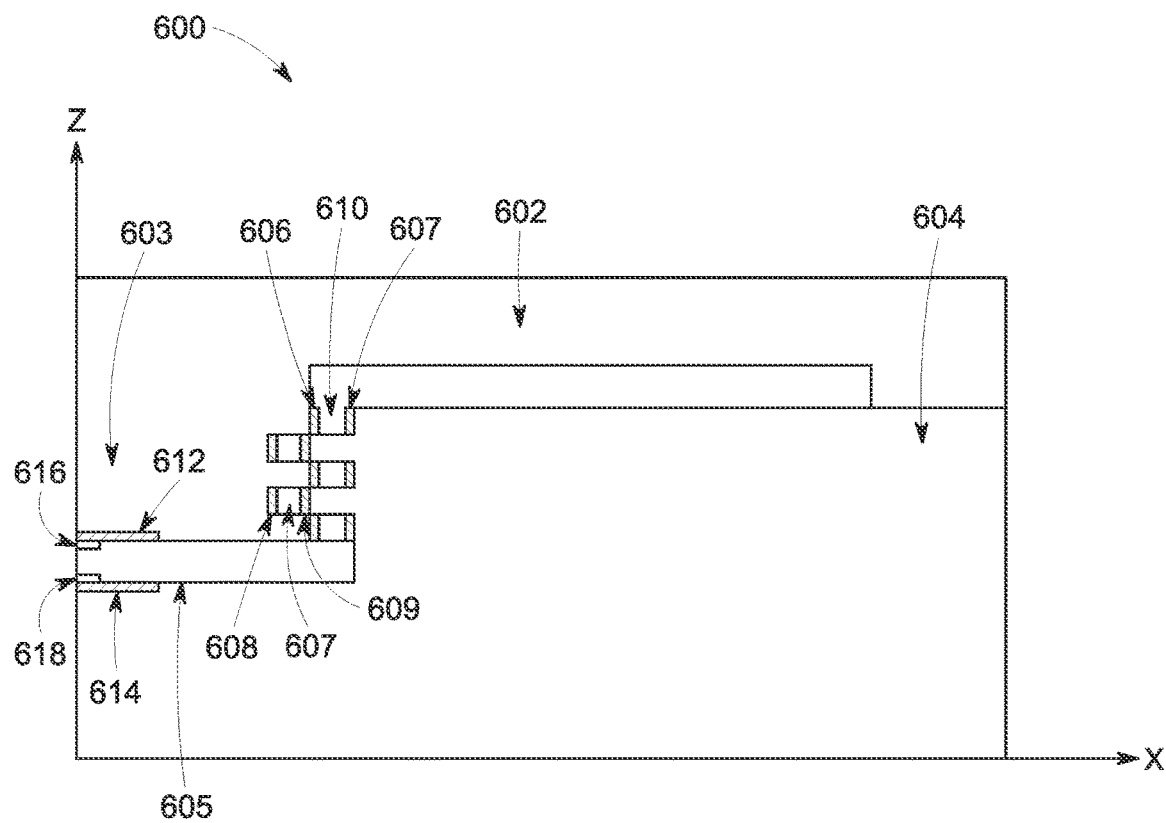
FIG. 6 illustrates another configuration for an example CMUT with dual out-of-plane and in-plane actuation and displacement, in accordance with various embodiments.

FIG. 6 illustrates another configuration for an example CMUT with dual out-of-plane and in-plane actuation and displacement, in accordance with various embodiments. Referring to FIG. 6, there is shown a CMUT 600 that is similar to the CMUT 200, except that the edges of the center mass 603 and the edges of the depression 605 are corrugated. Accordingly, the electrodes 606 and 607 are offset horizontally from the electrodes 608 and 609. There is a horizontal gap 610 between the electrodes 606 and 607 and between the electrodes 608 and 609. The corrugated edges may also be referred to as non-horizontal edges. The horizontal gap 610 may be referred to as the electrode gap 610. Similar to CMUT 200, the CMUT 600 includes horizontal or in-plane electrodes 612 and 614 and respective insulation layers 616 and 618.

Figure 7:
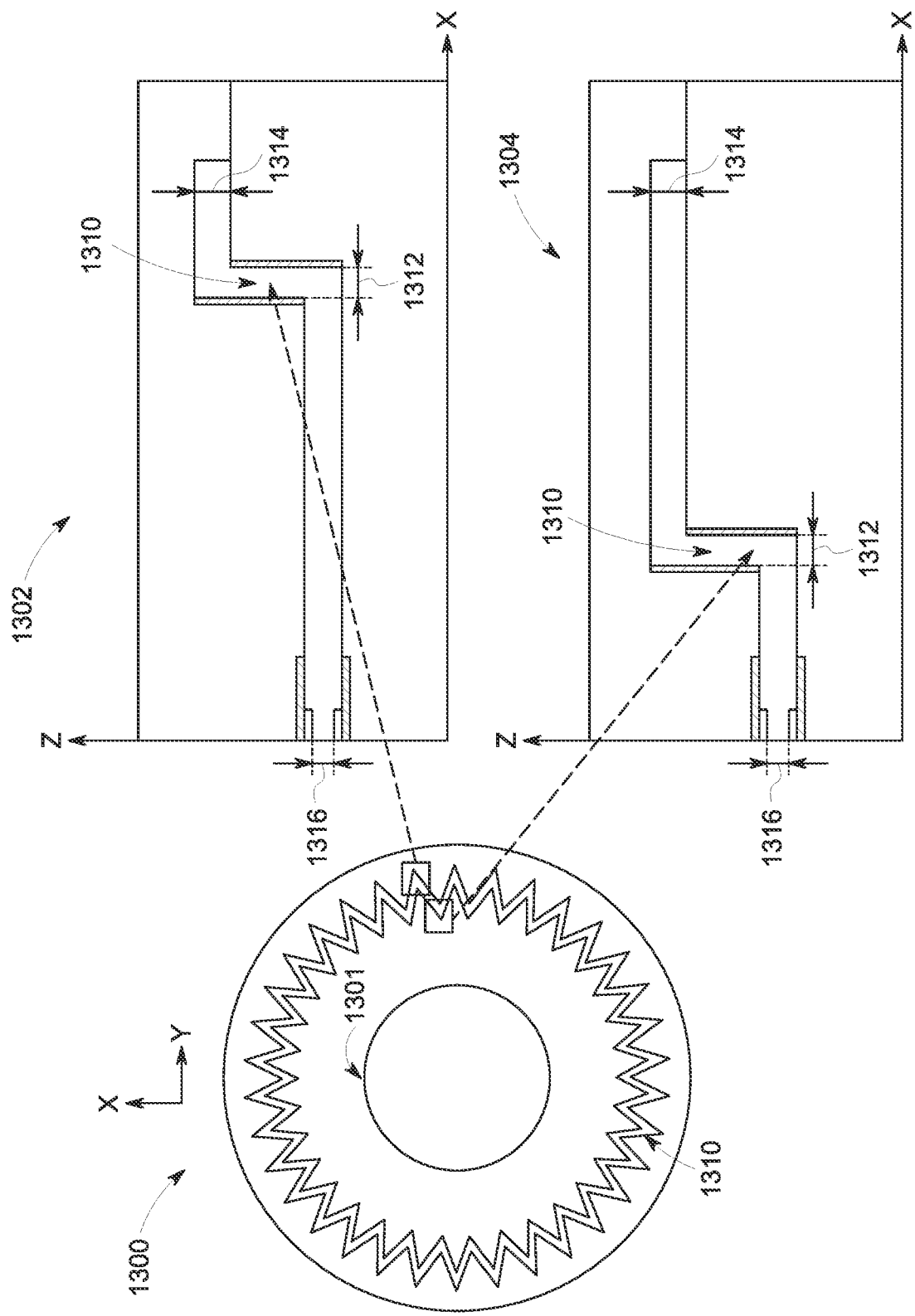
FIG. 7 illustrates another configuration for an example CMUT with dual out-of-plane and in-plane actuation and displacement, in accordance with various embodiments.

FIG. 7 illustrates another configuration for an example CMUT with dual out-of-plane and in-plane actuation and displacement, in accordance with various embodiments. Referring to FIG. 7, there is shown a top cross-sectional view (for example, X-Y plane) of a CMUT 1300 including an in-plane actuation electrode 1301 that shows a pattern of a horizontal gap 1310. There are also shown side cross-sectional views (for example, X-Z plane) 1302 and 1304 that show the horizontal gap 1312 between the electrodes (e.g., vertical or fringe electrodes), as well as the upper vertical gap 1314 and the lower vertical gap 1316 (e.g., between the in-plane or horizontal electrodes). The horizontal gap 1312 may be similar to the horizontal gap 306 in FIG. 3. The upper vertical gap 1314 may be similar to the upper vertical gap 307 in FIG. 3 and the lower vertical gap 1316 may be similar to the lower vertical gap 309 in FIG. 3. As can be seen, the cross-sectional view 1302 is for an outer portion of the horizontal gap 1310, and the cross-sectional view 1304 is for an inner portion of the horizontal gap 1310.

Figure 8:
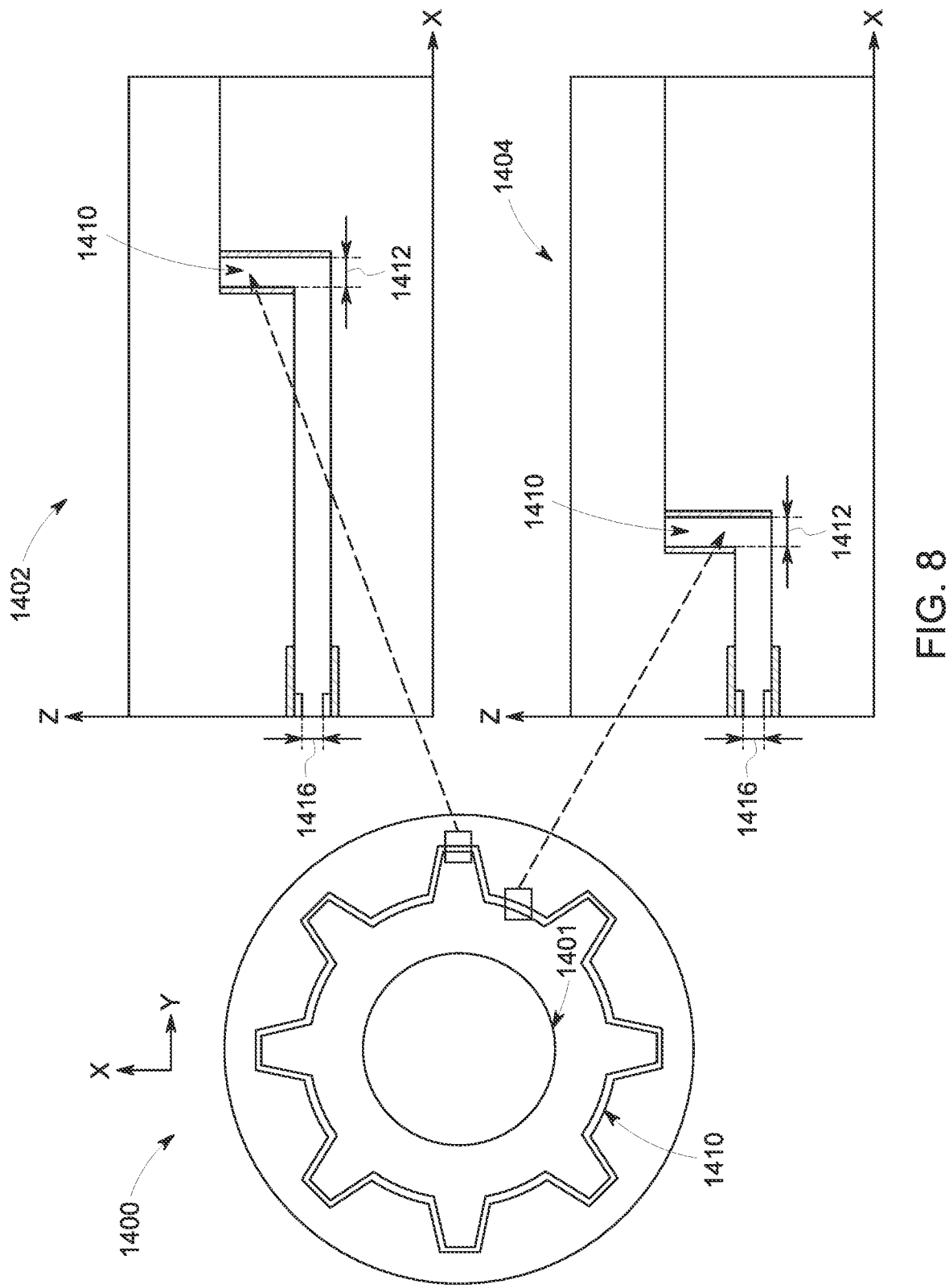
FIG. 8 illustrates another configuration for an example CMUT with dual out-of-plane and in-plane actuation and displacement, in accordance with various embodiments.

FIG. 8 illustrates another configuration for an example CMUT with dual out-of-plane and in-plane actuation and displacement, in accordance with various embodiments. Referring to FIG. 8, there is shown a top cross-sectional view (for example, X-Y plane) of a CMUT 1400 including an in-plane actuation electrode 1401 that shows a pattern of a horizontal gap 1410. There are also shown side cross-sectional views (for example, X-Z plane) 1402 and 1404 that show the horizontal gap 1412 between the electrodes (e.g., vertical or fringe electrodes), as well as the lower vertical gap 1416 (e.g., between the in-plane or horizontal electrodes). The horizontal gap 1412 may be similar to the horizontal gap 306 in FIG. 3. The lower vertical gap 1416 may be similar to the lower vertical gap 309 in FIG. 3. As can be seen, the cross-sectional view 1402 is for an outer portion of the horizontal gap 1410, and the cross-sectional view 1404 is for an inner portion of the horizontal gap 1410.

While two example configurations are shown for increasing the total surface area of electrodes that can be used for the horizontal gaps 1310 and 1410 of the CMUTs 1300 and 1400, respectively, a horizontal gap when seen from the top (for example, X-Y plane) may be any of various shapes such as, for example, a circle, an oval, a regular or irregular polygon, etc. The horizontal gap may be, for example, continuous as shown in FIGS. 7 and 8, one or more discrete pieces that together do not go all the way around a CMUT, or one or more discrete pieces that together go around a CMUT. Accordingly, when viewed from above (for example, the X-Y plane), the horizontal gap of a CMUT may comprise one or more gaps, where each gap may be any geometric shape with any pattern.

Additionally, any CMUT may have any geometric shape when viewed from the top (for example, the X-Y plane). For example, while the CMUTs 1300 and 1400 are shown to be circular, a CMUT may be elliptical, oval, a polygon, etc. Additionally, while several configurations were shown, various embodiments of the disclosure need not be so limited. For example, the CMUT 200 may have multiple electrodes 210 and 211 similar to the CMUT 600. That is, while the edges may be planar, there may be multiple electrodes may be multiple electrodes 210 and corresponding multiple electrodes 211. Or there may be a different number of electrodes 210 than electrodes 211, where, for example, multiple electrodes 210 may be used for a single electrode 211 or vice versa.

Additionally, the center mass 203, 503, 603, etc., may be different shapes than the examples disclosed. For example, the center mass 503 may have rounded (convex) edges and the depression 505 of the substrate 504 may have rounded (concave) edges so that the depression 505 may accept the center mass 503. Accordingly, various embodiments of the disclosure may have appropriately rounded electrodes 506 and 507.

However, the shape of a center mass and/or a depression of a substrate need not be limited to just what is mentioned in the disclosure. Rather, any appropriate shape may be used. Furthermore, the electrodes placed on the edge surfaces of a center mass and/or a depression may have conforming shapes to the edge surfaces or shapes that are different than the edge surfaces.

Additionally, while various descriptions were made of edges, surfaces, electrodes, the edge, surface, or electrode may be a single, continuous edge/surface/electrode. For example, when the center mass 203 is cylindrical, the center mass 203 may comprise a single vertical surface. Accordingly, there may be a single electrode 210 and a single electrode 211 for the CMUT 200. However, even when there is a single surface, there may be multiple electrodes 210 and multiple electrodes 211 placed at regular intervals along the single surface of the center mass 203 of the plate 202 and/or the single surface of the depression 205 of the substrate 204.

Furthermore, the gaps described in the various figures may be filled with fluid, such as, for example, air, or may comprise some level of vacuum. Accordingly, in various embodiments of the disclosure, the capacitive transducers may be configured such that the gaps are air-tight.

Figure 4:
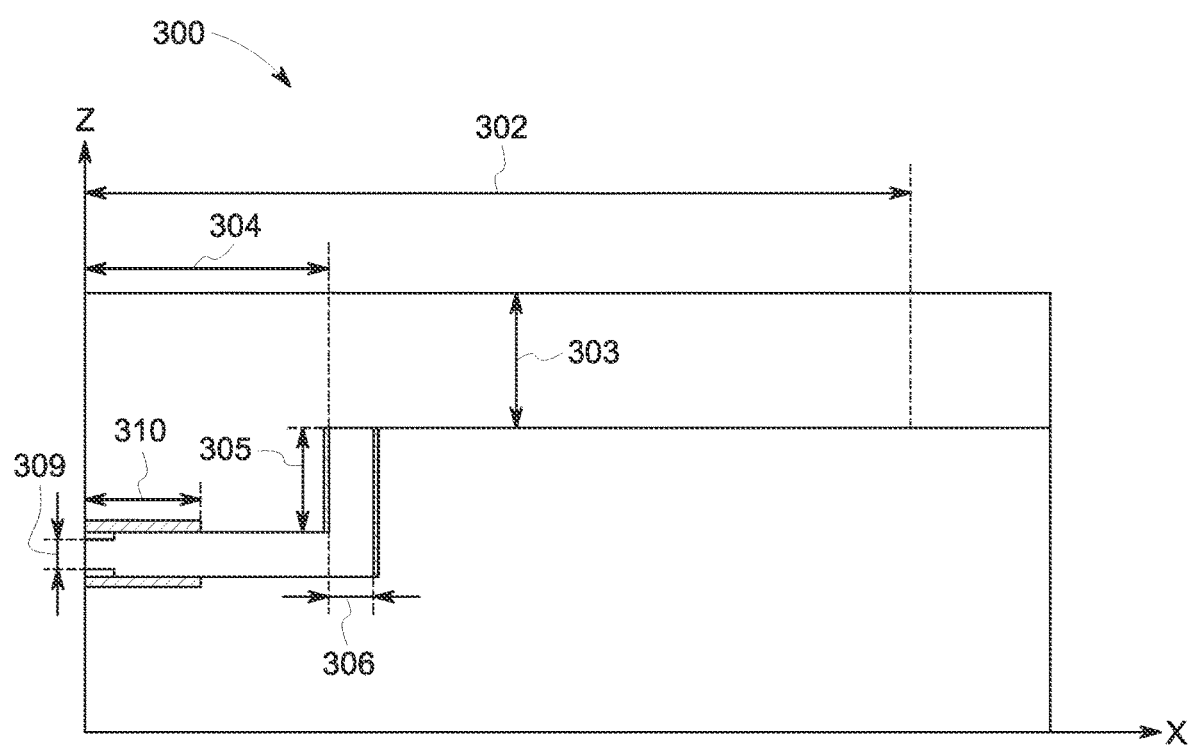
FIG. 4 illustrates example applicable dimensions of another CMUT, in accordance with various embodiments.
Figure 9:
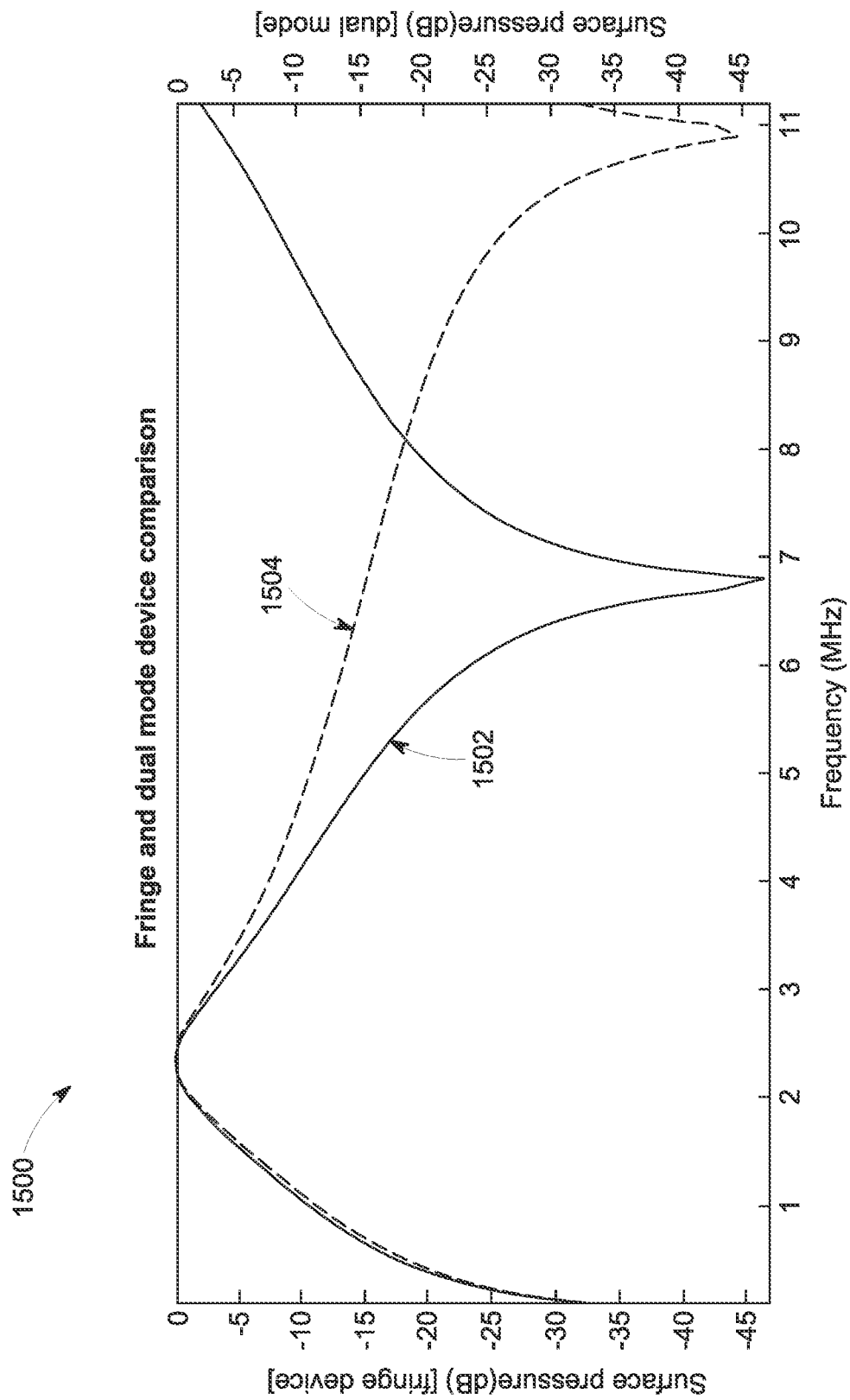
FIG. 9 illustrates an example graph comparing bandwidth of the CMUT of FIG. 4 during fringe mode activation and dual mode activation, in accordance with various embodiments.

FIG. 9 illustrates an example graph comparing bandwidth of the CMUT 350 of FIG. 4 during fringe mode activation and dual mode activation, in accordance with various embodiments. Referring to FIG. 9, there is shown a graph 1500 with frequency in megahertz (MHz) along the X-axis, surface pressure in decibels (dB) along the Y-axis on the left side of the graph 1500, and surface pressure in dB along the Y-axis on the right side of the graph 1500. Plot 1502 (e.g., shown as a solid plot) shows the transmit bandwidth of the CMUT 350 of FIG. 4 in fringe mode activation (e.g., both the DC bias and the AC signal are only applied to the vertical or fringe electrodes) relative the surface pressure indicated on the right of the graph 1500. Plot 1504 (e.g., shown as a dashed plot) shows the transmit bandwidth of the CMUT 350 of FIG. 4 in dual mode activation (e.g., DC bias applied to the vertical or fringe electrodes and the AC signal applied to the horizontal or in-plane electrodes). As depicted in FIG. 9, the transmit bandwidth of the CMUT 350 of FIG. 4 is considerably higher during dual mode activation due to the added electromechanical coupling with the AC actuation on the in-plane electrodes.

Figure 10:
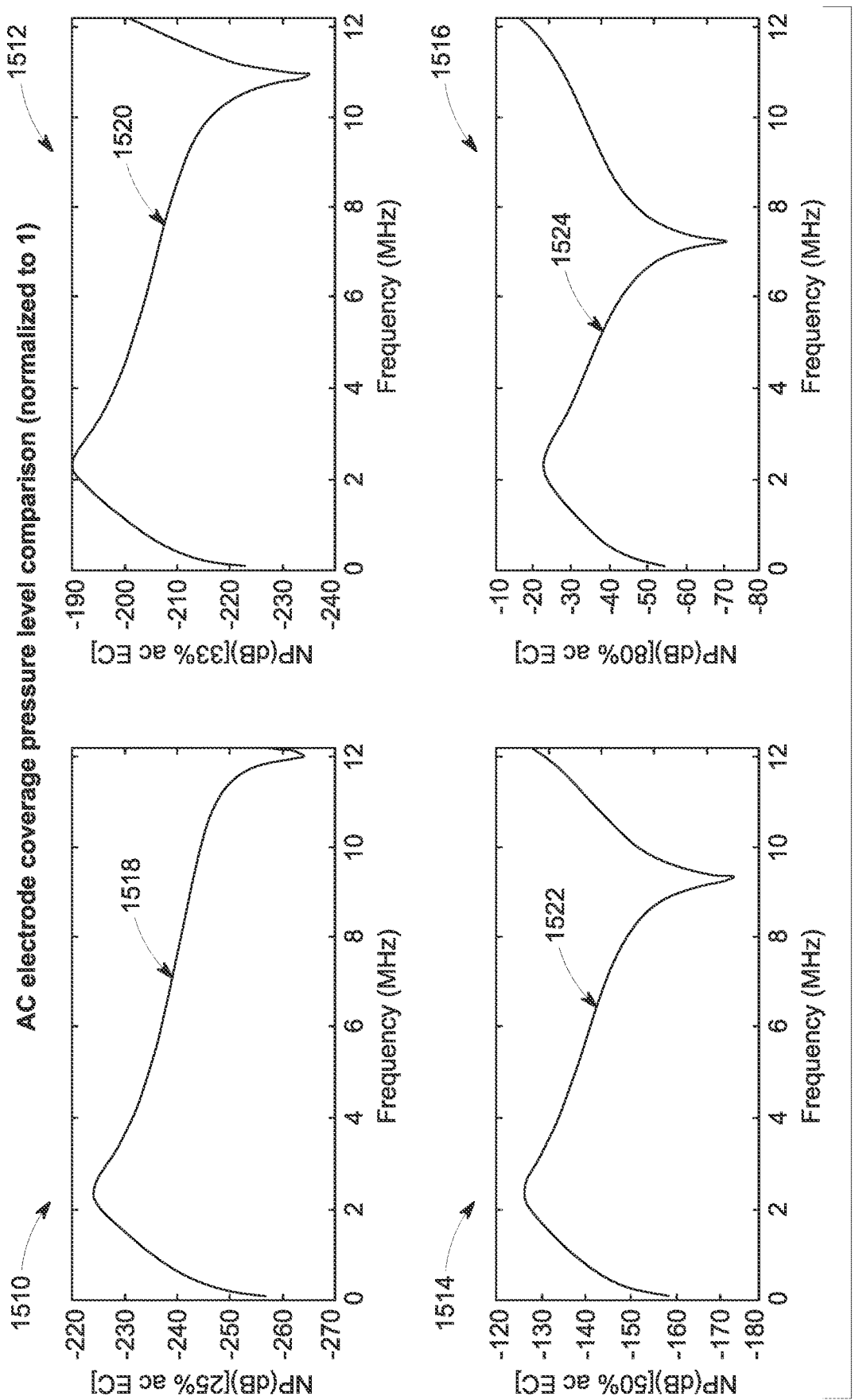
FIG. 10 illustrates an example series of graphs comparing the effect of in-plane electrode coverage for an example CMUTs during dual mode activation on pressure and bandwidth, in accordance with various embodiments.

FIG. 10 illustrates an example series of graphs comparing the effect of in-plane electrode (e.g., horizontal electrode with AC actuation) coverage for an example CMUT during dual mode activation on pressure and bandwidth, in accordance with various embodiments. Referring to FIG. 10, there are shown graphs 1510, 1512, 1514, and 1516 with frequency in MHz along the X-axis and normalized pressure (normalized to 1) along the Y-axis. The graphs 1510, 1512, 1514, and 1516 are for electrode coverage percentages (e.g., relative to the mass radius) of 25 percent, 33 percent, 50 percent, and 80 percent respectively. Plots 1518, 1520, 1522, and 1524 show the effect of in-plane electrode coverage on both pressure and bandwidth. For example, as electrode coverage increases the bandwidth decreases and the normalized pressure increases.

Figure 11:
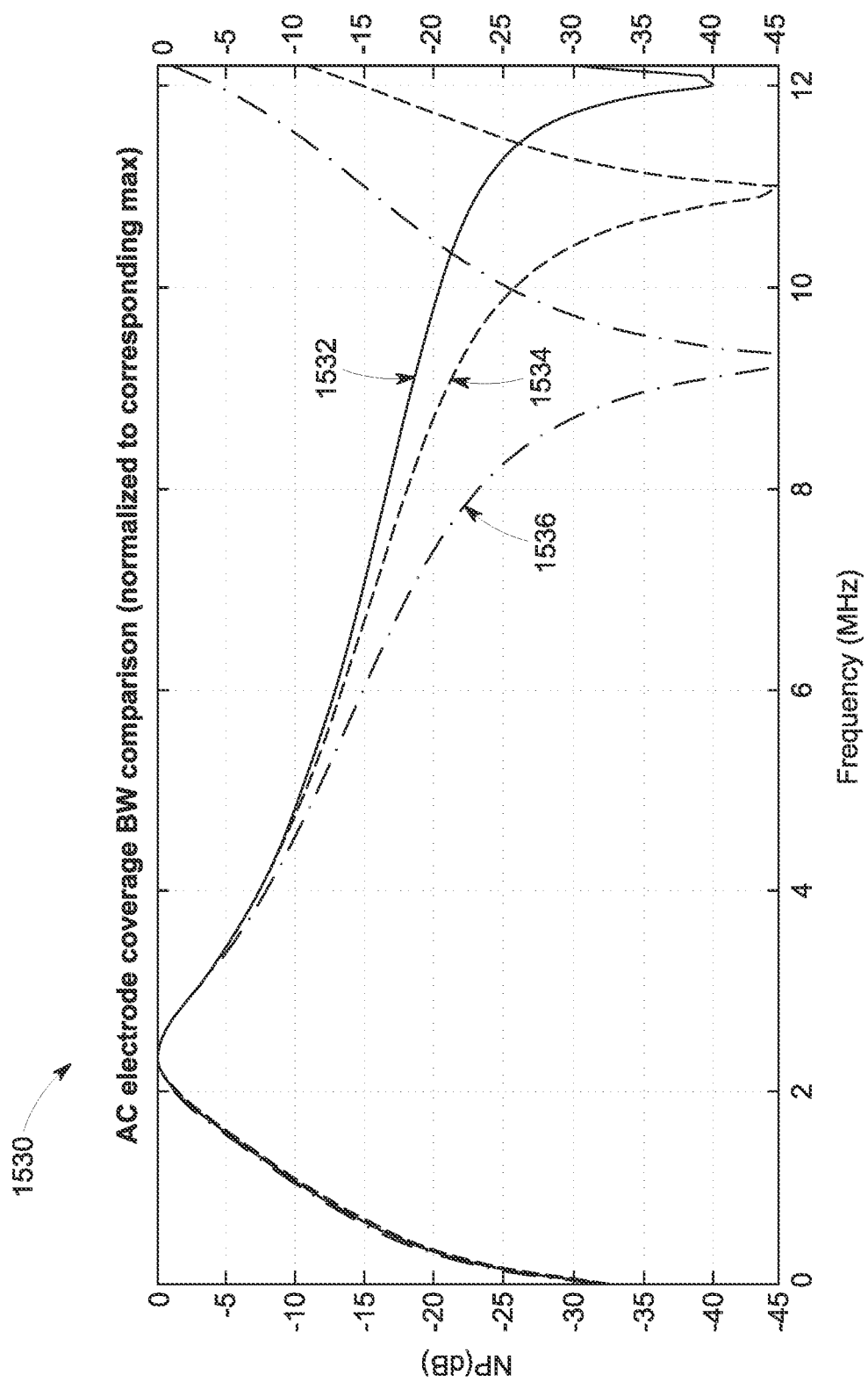
FIG. 11 illustrates an example graph comparing the effect of in-plane electrode coverage for example CMUTs during dual mode activation on pressure and bandwidth, in accordance with various embodiments.

Similarly, FIG. 11 illustrates an example graph comparing the effect of in-plane electrode (e.g., horizontal electrode with AC actuation) coverage for an example CMUT during dual mode activation on pressure and bandwidth, in accordance with various embodiments. Referring to FIG. 11, there is shown graph 1530 with frequency in MHz along the X-axis and normalized pressure (normalized to corresponding max) along the Y-axis. Plots 1532 (shown as solid plot), 1534 (shown as dashed plot), and 1536 (shown as dotted-dashed plot) are for electrode coverage percentages (e.g., relative to the mass radius) of 25 percent, 33 percent, and 50 percent, respectively. Plots 1532, 1534, and 1536 show the effect of in-plane electrode coverage on both pressure and bandwidth. For example, as electrode coverage increases the bandwidth decreases. As depicted in FIGS. 10 and 11 varying the in-plane electrode coverage areas enables optimization of the output power (e.g., acoustic power) and bandwidth.

Figure 12:
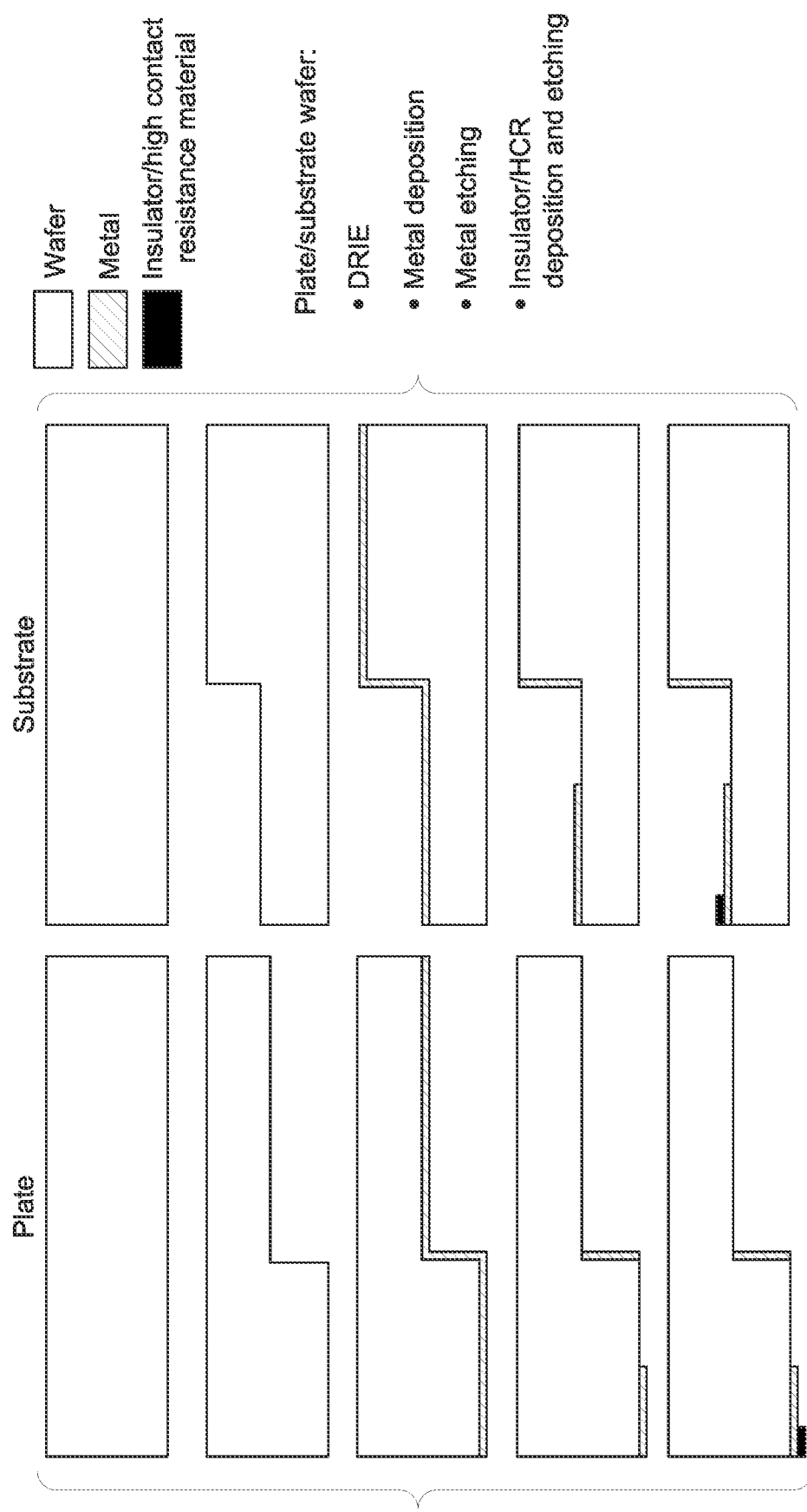
FIGS. 12 and 13 illustrate schematic diagrams illustrating manufacture of an example CMUT with dual out-of-plane and in-plane actuation and displacement, in accordance with various embodiments.
Figure 13:
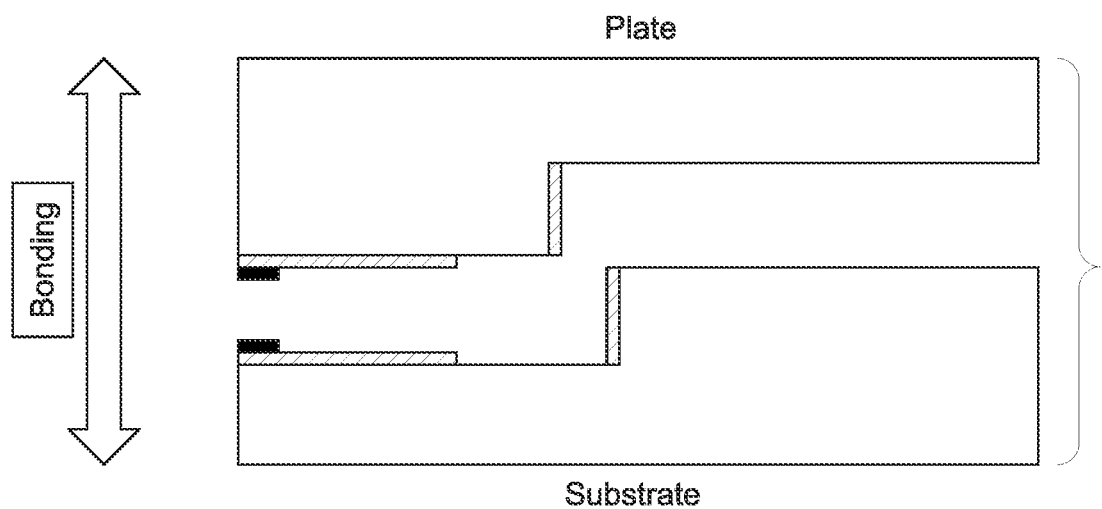

FIGS. 12 and 13 illustrate schematic diagrams illustrating manufacture of an example CMUT with dual out-of-plane and in-plane actuation and displacement, in accordance with various embodiments. In FIG. 12, the manufacturing of the plate and substrate with the vertical and horizontal electrodes discussed above are shown on the left and right, respectively, corresponding to FIG. 3. The various manufacturing steps are similar but the plate and substrate have complementary orientations. It should be noted that only portions of the plate and the substrate are shown and the components are not to scale. The plate and substrate may be subjected to other manufacturing steps besides those described below.

As depicted in FIG. 12, a wafer (e.g., silicon wafer) is subjected to etching (e.g., deep reactive-ion etching (DRIE)) to form the mass in the plate and the depression in the substrate. Following etching, metal, via metal deposition is deposited on the plate and substrates on the surfaces (e.g., horizontal and vertical surfaces) that will face each other. The metal is then subjected to metal etching to form the respective horizontal and vertical electrodes on the plate and the substrate. Following metal etching, insulation layers or high contact resistance material may be disposed on and etched on the in-plane or horizontal electrodes of the plate and the substrate. In certain embodiments, respective insulation layers are disposed on both the plate and the substrate. In other embodiments, an insulation layer is disposed on the plate only. In other embodiments, an insulation layer is disposed on the substrate only. Upon manufacturing the plate and the substrate with the electrodes and insulation layers, as depicted in FIG. 13, the plate and substrate are bonded together forming the CMUT (as well as the enclosed gap between the plate and the substrate) (e.g., corresponding to FIG. 3).

Technical effects of the disclosed subject matter include providing CMUTs with dual out-of-plane and in-plane actuation and displacement. In particular, a direct current (DC) signal may be applied to a pair of vertical electrodes (e.g., for out-of-plane actuation) and an alternative current signal applied to a pair of horizontal electrodes (e.g., for in plane actuation). Actuation with the DC signal is orthogonal to a direction of displacement of a center mass of a plate toward a depression of a substrate, while actuation with the AC signal is parallel to the direction of displacement. The in-plane actuation with the AC signal increases the electromechanical coupling factor in comparison to CMUT devices just having fringe electrodes. This enables the CMUTs to have a higher transmit bandwidth during dual mode activation when the DC signal is applied to the pair of vertical electrodes and the AC signal is applied to the pair of horizontal or in-plane electrodes as opposed to during fringe mode activation when both the AC and DC signals are applied to the vertical pair of electrodes. The disclosed CMUTs can operate in both a conventional mode of operation and a mechanical collapse mode of operation. In addition, the CMUTs can operate in either fringe mode activation or dual mode activation.

This written description uses examples to disclose the subject matter, including the best mode, and also to enable any person skilled in the art to practice the disclosed subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A capacitive transducer, comprising:
   a plate comprising a protruding center mass;
   a substrate with a center depression configured to accept the center mass;
   a first electrode coupled to a non-horizontal edge surface of the center mass;
   a second electrode coupled to a non-horizontal edge surface of the center depression;
   a third electrode coupled to a horizontal edge surface of the center mass; and
   a fourth electrode coupled to a horizontal edge surface of the center depression;
   wherein the plate is coupled to the substrate at least along an outer perimeter area of the plate and the substrate.

2. The capacitive transducer of claim 1, wherein the first and second electrodes are configured to be actuated via a direct current (DC) signal applied to the first and second electrodes and the third and fourth electrodes are configured to be actuated via an alternate current (AC) signal applied to the third and fourth electrodes.

3. The capacitive transducer of claim 1, wherein actuation with the DC signal is orthogonal to a direction of displacement of a bottom surface of the center mass of the plate toward a top surface of the center depression of the substrate, and wherein actuation with the AC signal is parallel to the direction of displacement.

4. The capacitive transducer of claim 1, wherein the capacitive transducer is configured to have a transmit bandwidth that is higher when a direct current (DC) signal is applied to the first and second electrodes and an alternate current (AC) signal is applied to the third and four electrodes as opposed to when both the AC and DC signals are applied to the first and second electrodes.

5. The capacitive transducer of claim 1, wherein the capacitive transducer is configured to operate in a transmit mode, a receive mode, and a transmit and receive mode.

6. The capacitive transducer of claim 5, wherein during operation in the transmit mode only an alternate current signal is applied to the third and fourth electrodes and a current signal is not applied to the first and second electrodes.

7. The capacitive transducer of claim 5, wherein during operation in the transmit and receive mode a direct current (DC) signal is applied to the first and second electrodes and an alternate current (AC) signal is applied to the third and fourth electrodes during transmission and both the AC and DC signals are applied to the third and fourth electrodes during receiving.

8. The capacitive transducer of claim 7, wherein during operation in the transmit and receive mode a voltage level of the DC signal is different during transmission compared to during receiving.

9. The capacitive transducer of claim 1, comprising a first insulation layer disposed on a portion of the third electrode, a second insulation layer disposed on a portion of the fourth electrode, or both the first insulation layer disposed on the portion of the third electrode and the second insulation layer disposed on the portion of the fourth electrode.

10. The capacitive transducer of claim 1, comprising a horizontal gap between the first and second electrodes and a vertical gap disposed between the third and fourth electrodes.

11. The capacitive transducer of claim 1, wherein the non-horizontal edge surface of the center mass and the non-horizontal edge surface of the center depression are substantially vertical surfaces.

12. The capacitive transducer of claim 1, wherein the non-horizontal edge surface of the center mass and the non-horizontal edge surface of the center depression are angled surfaces.

13. The capacitive transducer of claim 1, wherein the horizontal edge surface of the center mass and the non-horizontal edge surface of the center depression are substantially horizontal surfaces.

14. The capacitive transducer of claim 1, wherein the non-horizontal edge surface of the center mass and the non-horizontal edge surface of the center depression are rounded surfaces.

15. The capacitive transducer of claim 1, wherein the non-horizontal edge surface of the center mass and the non-horizontal edge surface of the center depression are corrugated surfaces.

16. A system, comprising:
a capacitive transducer comprising:
a plate comprising a protruding center mass;
a substrate with a center depression configured to accept the center mass;
a first pair of electrodes arranged on non-horizontal surfaces of the capacitive transducer; and
a second pair of electrodes arranged on horizontal surfaces of the capacitive transducer; and
circuitry configured to actuate the capacitive transducer by applying a direct current (DC) signal to the first pair of electrodes and applying an alternative current (AC) signal to the second pair of electrodes.

17. The system of claim 16, wherein actuation with the DC signal is orthogonal to a direction of displacement of a bottom surface of the center mass of the plate toward a top surface of the center depression of the substrate, and wherein actuation with the AC signal is parallel to the direction of displacement.

18. The system of claim 16, wherein the first pair of electrodes comprises a first electrode coupled to a non-horizontal edge surface of the center mass and a second electrode coupled to a non-horizontal edge surface of the center depression, and wherein the second pair of electrodes comprises a third electrode coupled to a horizontal edge surface of the center mass and a fourth electrode coupled to a horizontal edge surface of the center depression.

19. A capacitive transducer, comprising:
a plate comprising a protruding center mass;
a substrate with a center depression configured to accept the center mass;
a first electrode coupled to a non-horizontal edge surface of the center mass;
a second electrode coupled to a non-horizontal edge surface of the center depression;
a third electrode coupled to a horizontal edge surface of the center mass;
a fourth electrode coupled to a horizontal edge surface of the center depression; and
a first insulation layer disposed on a portion of the third electrode, a second insulation layer disposed on a portion of the fourth electrode, or both the first insulation layer disposed on the portion of the third electrode and the second insulation layer disposed on the portion of the fourth electrode.

20. The capacitive transducer of claim 19, wherein during operation actuation of the capacitive transducer a direct current signal applied to the first and second electrodes is orthogonal to a direction of displacement of a bottom surface of the center mass of the plate toward a top surface of the center depression of the substrate and an applied current signal applied to the third and fourth electrodes is parallel to the direction of displacement.

* * * * *